US008655042B2

(12) United States Patent
Florent

(10) Patent No.: US 8,655,042 B2
(45) Date of Patent: Feb. 18, 2014

(54) DEVICE SIZING SUPPORT DURING INTERVENTIONS

(75) Inventor: Raoul Florent, Ville Davray (FR)

(73) Assignee: Koninklijke Philips N.V., Eindhoven (NL)

( * ) Notice: Subject to any disclaimer, the term of this patent is extended or adjusted under 35 U.S.C. 154(b) by 109 days.

(21) Appl. No.: 13/321,378

(22) PCT Filed: Jun. 17, 2010

(86) PCT No.: PCT/IB2010/052723
§ 371 (c)(1),
(2), (4) Date: Nov. 18, 2011

(87) PCT Pub. No.: WO2010/150145
PCT Pub. Date: Dec. 29, 2010

(65) Prior Publication Data
US 2012/0082360 A1    Apr. 5, 2012

(30) Foreign Application Priority Data
Jun. 23, 2009   (EP) .................................... 09305588

(51) Int. Cl.
*G06K 9/00* (2006.01)
(52) U.S. Cl.
USPC ............................................ 382/132; 378/20
(58) Field of Classification Search
None
See application file for complete search history.

(56) References Cited

U.S. PATENT DOCUMENTS

| | | | |
|---|---|---|---|
| 4,217,854 A * | 8/1980 | Brown ........................... | 118/504 |
| 5,253,653 A | 10/1993 | Daigle et al. | |
| 6,620,111 B2 | 9/2003 | Stephens et al. | |
| 6,620,114 B2 | 9/2003 | Vrba et al. | |
| 7,239,733 B2 * | 7/2007 | Abe et al. ...................... | 382/132 |
| 7,458,977 B2 * | 12/2008 | McGinley et al. ............ | 606/130 |
| 2003/0081716 A1 | 5/2003 | Tumer | |
| 2003/0088195 A1 | 5/2003 | Vardi et al. | |
| 2004/0133129 A1 | 7/2004 | Harari et al. | |
| 2006/0058643 A1 * | 3/2006 | Florent et al. ................. | 600/423 |
| 2009/0097725 A1 | 4/2009 | Krupnik et al. | |

FOREIGN PATENT DOCUMENTS

| | | | |
|---|---|---|---|
| EP | 1768068 A2 | 3/2007 | |
| GB | 2355797 A | 5/2001 | |
| WO | 03049794 A1 | 6/2003 | |
| WO | 2006103644 A1 | 10/2006 | |
| WO | 2008104909 A1 | 9/2008 | |

OTHER PUBLICATIONS

Jorg Bredo et al, "Algorithmic Solutions for Live-Device-To-Vessel Match", In Proceedings of SPIE, vol. 5370, Medical Imaging 2004, May 2004, pp. 1486-1497.

(Continued)

*Primary Examiner* — Bhavesh Mehta
*Assistant Examiner* — Siamak Harandi

(57) ABSTRACT

The invention relates to a method and an apparatus for providing device sizing support, the method comprising obtaining an X-ray image of a vessel, introducing a guide wire having a radiopaque wire tip into the vessel, obtaining an X-ray image of the wire tip, segmenting the wire tip when it passes through the vessel, and providing sizing information relating to the size of the vessel based on the size of the wire tip. The imaging system according to the invention includes means providing functionality for performing the method according to the invention.

13 Claims, 2 Drawing Sheets

Figure 1:
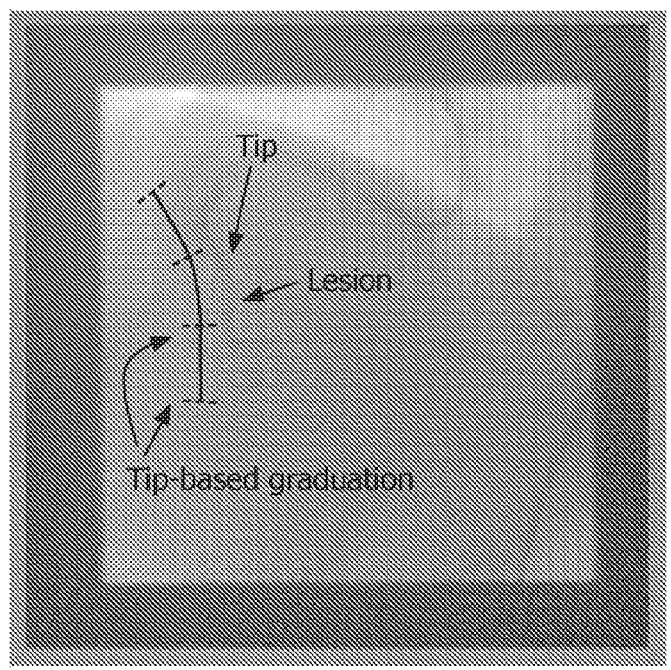

Bended ruler overlay in the fluoroscopic image at stenosis passing time

(56) References Cited

OTHER PUBLICATIONS

Onno Wink et al, "Intra-Procedural Coronary Intervention Planning Using Hybrid 3-Dimensional Reconstruction Techniques", Academic Radiology, vol. 10, Issue 12, pp. 1433-1441, Dec. 2003.

Kaoru Tanaka et al, "The Accuracy of Length Measurements Using Different Intravascular Ultrasound Motorized Transducer Pullback Systems", The International Journal of Cardiovascular Imaging, vol. 23, No. 6, Dec. 2007, pp. 733-738.

* cited by examiner

Bended ruler overlay in the fluoroscopic image at stenosis passing time

Bended ruler overlay in a corresponding angiographic image
(the tip is not the way)

Two scenario of realisation (overlay in passing-time image VS in tip-less image)

DEVICE SIZING SUPPORT DURING INTERVENTIONS

The invention relates to providing device sizing support during medical interventions, e.g. percutaneous coronary interventions. As explained in detail below, determining the appropriate size of an intervention device like, for example, a balloon or a stent is an important task and is crucial for a successful intervention.

An example for the field in which the invention may be used is an imaging system for PCI (Percutaneous Coronary Intervention) in catheter laboratories, to treat cardiac stenoses. A description of the basic interventional procedure can be found in [1]:

"After a catheter is inserted into the vascular system at an access site, it is advanced along large vessels to the vascular structure that requires treatment. Contrast agent is injected via the catheter and cathlab x-ray equipment records an angiographic sequence that shows the vessels when filled with contrast agent. The diagnostic angiogram acquisitions can be repeated with varying imager geometries. Diagnosis and intervention planning are based on such diagnostic angiograms ( . . . ). During intervention, a flexible, partially or fully radio-opaque guidewire is advanced to the affected vascular structures (e.g. stenoses in coronaries, neurovascular aneurisms, or arterio-venous malformations). Fluoroscopic low-dose x-ray surveillance visualizes the guidewire ( . . . ) and allows for the hand-eye-coordination of the interventionalist while advancing the guidewire. When positioned, the guidewire serves as rail to deliver interventional devices (e.g. balloons for dilation and stent delivery, detachable coils for aneurysm clotting). The delivery and deployment of the interventional devices is also fluoroscopy-controlled."

In PCI, a very crucial point lies in the correct sizing of the intervention devices such as the balloon or the stent. In particular determining the correct length of the stent is very important. A too short stent does not cover the full lesion and might injure the plaque at its extremity (edge effect, predisposing to restenosis). On the other hand, a too long stent might overlap with undesirable structures (another stent, a side-branch root, etc . . . ). In fact, there is a lot of literature, study and guidelines about the ideal length strategy during PCI and this may vary with the kind of stent used (bare metal or drug eluting). However, the bottom line is that determining the right stent length is indeed a key issue.

Basically the cardiologist determines the stent length primarily from the length of lesion (the stent should entirely cover the lesion). However, the length of lesion as seen under X-ray in an angiographic sequence (including contrast agent injection) is difficult to exploit mainly because of the foreshortening effect: only a projection of the lesion is available, and depending on the 3D spatial orientation of the lesion with respect to the projection plane orientation, the observed length might be substantially reduced.

Two main solutions for accurate length measuring are however possible:
  Use of an intra-vascular device such as intravascular ultrasound (IVUS) [2].
  Use of several angiographic views coupled with a reconstruction or modelling software to produce a 3D representation of the lesion on which quantitative measurement algorithms can be applied [3].
However, none of those solutions is ideal:
  IVUS is costly, not necessary reimbursed, and not necessary easily passed through the stenosis (which constitutes an additional risk to the intervention). For those reasons, IVUS is usually not considered for the sole task of device sizing. It is used preferably in those countries where it is reimbursed and only on specific interventions (usually involving large vessel segment such as the Left Main).
  3D representation is more or less heavy (from 2 view coronary modelling to full rotation for coronary reconstruction). But even the lightest of those procedures (2-view-modelling) is in practice very little used for length estimation. In particular, this is due to their disruptive nature with respect to the usual workflow. They indeed involve image transfer on a workstation, multi-acquisition or a rotational scan, and they often cannot be controlled from the table side. They therefore seem overly complex for the simple sake of lesion length estimation.

U.S. Pat. No. 6,620,114 B2 discloses a guide wire that can be placed in a patient's vasculature or body cavity. The guide wire includes one or more radiopaque markers that can be visualized by fluoroscopy or the like. The markers are preferably spaced apart longitudinally along the guide wire such that the markers and/or spaces between the markers can be used to make measurements of anatomical or artificial structures within the body.

U.S. Pat. No. 5,253,653 A discloses a guidewire assembly for measuring the size of occlusions in blood vessels which includes a guidewire having a flexible, distal end disposable in a blood vessel. The guidewire has a core wire disposed within it which extends to the distal tip. A linear array of radiopaque markers is disposed adjacent the distal tip of the core wire. The markers are spaced from each other at predetermined distances, whereby to enable the user to accurately measure the size and diameter of occlusions in blood vessels using radiological techniques.

GB 2,355,797 A discloses a guidewire or like device (such as a balloon catheter) for arterial angioplasty, calibrated so as to provide marker positions along at least part of its length, the marker positions or the spacing between them being radio-opaque or radio-lucent for radiographic detection and reading.

WO 03/049794 A1 suggests an apparatus and a method for gauging for accurately assisting in determining the length and size of a suitable stent to be deployed. The distal end of a catheter is furnished with a series of radio-opaque markings in an arrangement which makes for case of determination of length of stent to be used. The markings also aid in the determination of the size of the stent. The distal end of the same gauging catheter is bulleted to simulate the profile of a stent and balloon assembly for this purpose.

US 2003/0088195 A1 discloses an apparatus and methods for manufacturing a guidewire having a plurality of radiopaque markers. In a preferred embodiment, a guidewire is provided having a tapered distal section comprising a plurality of gold markers that are deposited on the guidewire at predetermined intervals, so that the outer surface of the guidewire is substantially smooth. The gold markers provide a fluoroscopic reference for positioning the guidewire and enable accurate sizing of vessel features, such as the length of a lesion.

The object of the invention is to provide an improved support to device sizing for a medical intervention.

The invention is indicated in the independent claims. Advantageous embodiments of the invention are indicated in the dependent claims.

One of the major advantages of the invention is to offer a table-side-controlled support to PCI device sizing and in particular to device length estimation. This support will help the cardiologist to accurately figuring out the size of the lesion (hence of the device) in question, in a way that will be fast and robust to foreshortening.

The invention enables to capture the size of the lesion relatively to the so-called wire-tip that is passed through the lesion before device sizing is needed. The wire-tip is very easily identifiable since it appears as a short very radio-opaque wire segment whose length is normalized and known. The basic idea is on the one hand to produce an enhanced view of the wire-tip at the precise instant where the stenosis is passed (the lesion is made visible with a little contrast-agent puff or obtained from roadmapping means), and on the other hand to produce quantitative (but essentially relative) sizing information that will be used to estimate the lesion extent. For instance, this view might contain an overlaid bended ruler parallel to the wire-tip and graduated in fraction of the wire-tip length to which the lesion should be compared.

Because the tip is within the lesion, any relative measurement between both objects is immune to foreshortening. Because this view is automatically produced, and its exploitation is click-less, its exploitation can be made from the table side.

The tip-scaled ruler (tip-length-based graduation) can be overlaid in various images and not necessary in the view where the tip was segmented and the bended ruler computed:

a) It can indeed be overlaid in an enhanced view computed from the fluoro sequence that captures both the tip and the stenosis seen with a little contrast agent.

b) It can be overlaid in a section of a fluoro sequence where a contrast agent puff has occurred but before the tip has entered the stenosis.

c) It can be overlaid in a corresponding angiographic image.

For option 'b', an additional intra-fluoro image registration is needed so as to overlay the ruler at approximately the right location (note that this location does not need to be accurately estimated since only relative length comparison is meaningful). For option 'c', roadmapping means can be exploited so as to determine which angio image and at approximately which location one should overlay the ruler. The major advantage of options 'b' and 'c' is that the tip is not in the way, and the comparison of the lesion with the ruler is easier.

Additionally, one might also display an estimation of the foreshortening local to the lesion or even more, possibly an estimation of the angle in the $3^{rd}$ dimension. This can be computed from the comparison of the tip size and of the observed size (in mm). For angle determination, simple rules relating to the acquisition geometry and the location of the tip can be used to solve orientation ambiguity.

Figure 2:
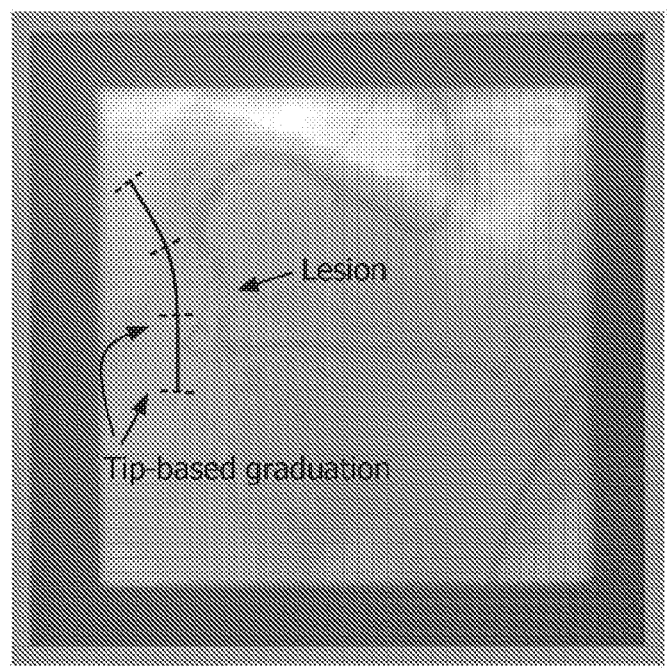
Figure 3:
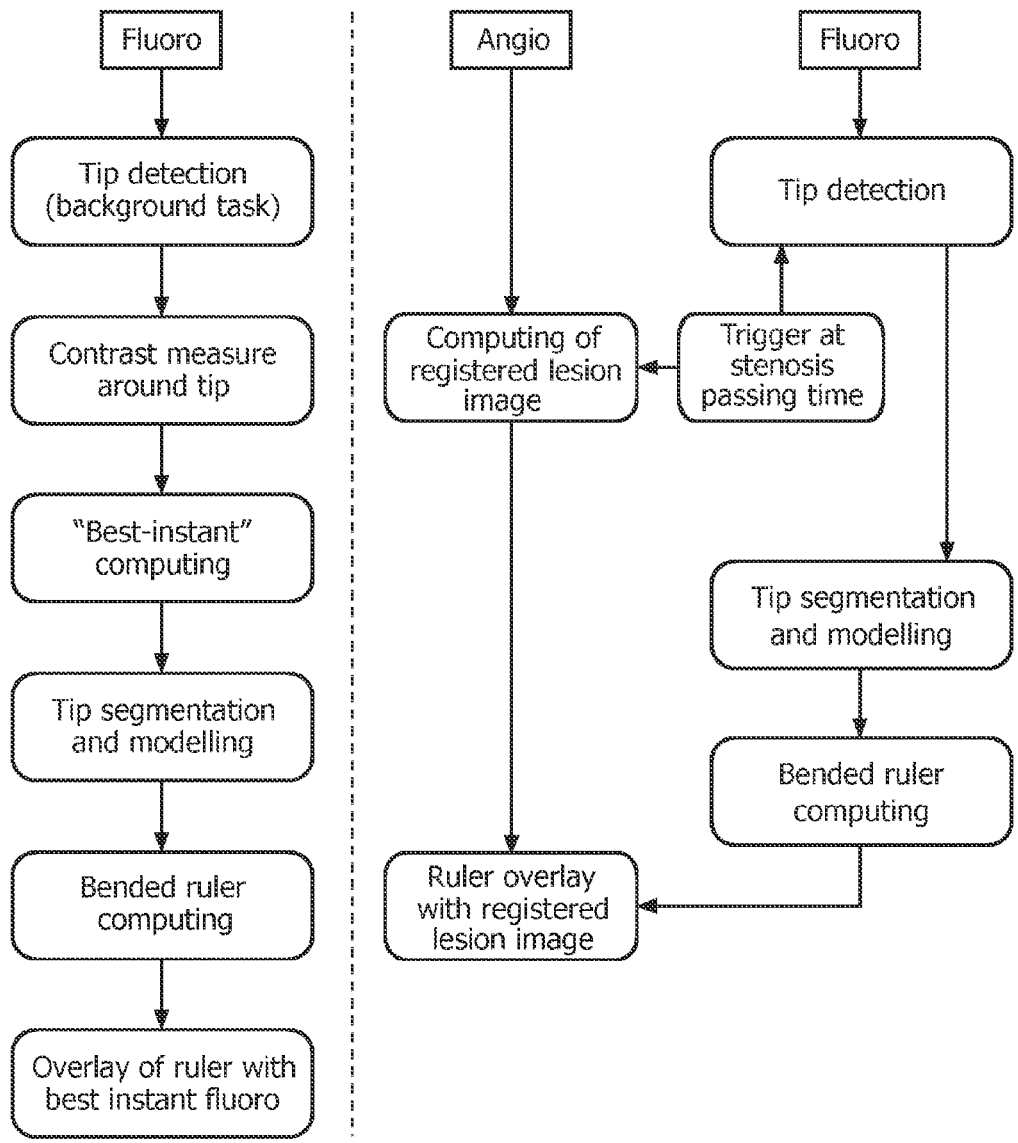

The invention will be described with more details below based on the attached figures, wherein FIGS. 1 and 2 show examples of the expected results; and
FIG. 3 shows two scenarios of realization.

In FIG. 1, the computed ruler is shown on top of a fluoroscopic image at a stenosis passing time (with a contrast agent puff). This refers to option 'a' introduced in the previous section.

In FIG. 2, the computed ruler is shown on top of an angiographic image (the tip is not in the way). The correspondence between the fluoro image, in which the tip was segmented (and the ruler computed) and this angio graphic image can be deduced for instance from a cardiac roadmapping technique as described in [4]. This refers to the option 'c' of the previous section.

In order to obtain this kind of results, several steps are needed as described in FIG. 3. This figure illustrates both option 'a' and 'c' (option 'b' is a variation of option 'c').

FIG. 3 shows two realization scenarios, i.e. an overlay in a passing-time image and an overlay in a tip-less image.

In the first scenario shown in FIG. 3, a fluoro image is taken. Detection of the tip of the guidewire is performed as a background task. Then the contrast is measured around the tip, followed by a "best-instant" computing. The wired tip is segmented and modelled, followed by computing a bended ruler. Then, an overlay of the ruler with the best instant flouro image is performed.

Another procedure shown in FIG. 3 involves detecting a tip in a fluoro image; triggering is performed at that instant of time when the tip passes a stenosis. Then the tip is segmented and modelled, and a corresponding bended buler is computed. The ruler is overlayed with a registered lesion image.

A third approach schematically depicted in FIG. 3 concerns an angiographic image. A registered lesion image is computed, based on a trigger at stenosis passing time. Then the ruler is overlayed with a registered lesion image.

For option 'a', several steps may be employed.

The wire-tip detection or tracking in a background task. Thanks to its very high X-ray absorbing nature and its limited length, this detection process is fairly easy and can be undertaken with conventional ridge enhancement and thresholding techniques. This approach can even be underpinned by ridge tracking techniques. In any case, this background task is to provide a segmentation of the tip at each frame of the current fluoroscopy run.

Once contrast has been produced through the injection catheter, it rapidly reaches the tip's vicinity. The continuous segmentation of the tip provides the geometry of the area where contrast is to be looked for and analysed. Typically the grey-level values around and on the tip are monitored, thus producing several time-intensity curves (for instance one curve for the average grey-level on the tip (along time), and one for the average on both sides of tip). This enables the determination of the optimal instant where both the tip and lesion are optimally visible.

For the selected instant, the tip is then carefully segmented and modelled (for instance as a spline curve). This can be achieved with traditional segmentation and curve fitting tools.

One can then produce a ruler model that is basically made of a curve parallel to the tip curve and containing graduation computed from the tip-length as observed in the current projection.

The bended ruler can then be overlaid next to the actual tip+lesion, thus providing the clinician with the ability to estimate the lesion length as a fraction or multiple of the tip length, and this irrespective of the possible foreshortening.

For option 'c', in addition to the already described steps, the following is necessary:

Somehow, the stenosis passing-time is indicated or detected. In its simplest version a trigger signal can simply be derived from a push button activated at the right instant. In a more complex version, roadmapping images could be used (see [4]) and the lesion (in the roadmap image) detected in the vicinity of the tip (in the fluoro image). When the tip gets near an actual lesion, a trigger signal can then be emitted.

The trigger signal designates a reference fluoro image and correlatively a reference position of the tip in this image. Using correspondence and registration means as involved in roadmapping (see [4]), it is then possible to find, to this fluoro reference fluoro image a matching angio image (called the registered lesion image), and to determine the motion to be applied to the reference tip location so that it fits to the angio image.

With those pieces of information it is then possible to produce the overlay of the bended ruler (computed in the same way as previously, but at the fluoro instant designated by the trigger signal) to the corresponding angio image, and at the right location.

There are many other extensions and variations of the invention as outlined below.

As already pointed out, the registered lesion image can be computed from a fluoro image with a contrast agent puff and before the tip enters in the stenosis. This simplifies the building and registration of the lesion image.

If the tip length is somehow entered in the system (there are very little possibilities for the value of this length), then converting pixels to millimeters and measuring the tip length in the image, one is capable of determining and displaying the estimated foreshortening degree. This simply amounts to compare the expected to the observed length.

In addition, the $3^{rd}$ dimension angle can even be determined in the same way.

In order to remove the usual angle ambiguity, simple rules relating to the acquisition geometry and the location of the tip can be involved.

The imaging system according to the present invention may be based on a conventional imaging system which is suitably modified or adapted by comprising means for obtaining sizing information according to the method of the present invention. The imaging system may include computing means for computing a virtual ruler. The imaging system may also comprise display means for displaying the ruler in an overlay view.

In other words, the imaging system according to the present invention may be based on a conventional imaging system suitably modified by means providing the functionality for executing the method according to the invention.

The invention may be applied to a cardiac system in PCI interventions. Due to the importance of this kind of interventions and the importance of accurate device sizing, the invention impact is very broad.

References:
[1] "Algorithmic Solutions for Live Device-to-Vessel Match", J. Bredno, B. Martin-Leung & K. Eck. In Proceedings of SPIE-Volume 5370-Medical Imaging 2004. Image Processing, J. Michael Fitzpatrick, Milan Sonka, Editors, May 2004, pp. 1486-1497
[2] "The accuracy of length measurements using different intravascular ultrasound motorized transducer pullback systems". K. Tanaka, S. G. Carlier, etc . . . The International Journal of Cardiovascular Imaging (formerly Cardiac Imaging). Volume 23, Number 6/December 2007
[3] Intra-procedural coronary intervention planning using hybrid 3-dimensional reconstruction techniques. Academic Radiology, Volume 10, Issue 12, Pages 1433-1441
[4] "Algorithmic Solutions for Live Device-to-Vessel Match", J. Bredno, B. Martin-Leung & K. Eck. In Proceedings of SPIE-Volume 5370-Medical Imaging 2004: Image Processing, J. Michael Fitzpatrick, Milan Sonka, Editors, May 2004, pp. 1486-1497
[5] U.S. Pat. No. 6,620,111 B2 (2003)
[6] U.S. Pat. No. 5,253,653 A (1993)
[7] GB 2 355 797 A (2001)
[8] WO 03/049794 A1 (2003)
[9] US 2003/0088195 A1 (2003)

The invention claimed is:

1. A method of providing support to percutanerous coronary intervention (PCI) device sizing of a lesion in an imaging system, the method comprising acts of:
   introducing a guide wire having a radiopaque wire tip into a vessel;
   obtaining an X-ray fluoro image of the wire tip from the imaging system;
   performing on a computing device acts of:
      detecting the wire tip on the X-ray fluoro image;
      segmenting and modeling the wire tip when it passes through the vessel;
      computing a virtual ruler; and
      overlaying the computed virtual ruler with a first image; and
   providing sizing information of the lesion.

2. The method according to claim 1, wherein the X-ray fluoro image of the wire tip is an enhanced view of the wire tip.

3. The method according to claim 1, after the act of detecting the wire tip further comprising acts of:
   measuring contrast around the wire tip; and
   computing a best-instant flouro image when the lesion is made visible,
   wherein the first image is the best-instant flouro image.

4. The method according to claim 1, wherein the computed virtual ruler is graduated in fractions of a length of the wire tip.

5. The method according to claim 4, wherein the computed virtual ruler is a bended ruler.

6. The method according to claim 1, after the act of detecting the wire tip further comprising acts of:
   indicating when the wire tip passes stenosis; and
   registering a lesion image,
   wherein the first image is the registered lesion image.

7. The method according to claim 1, wherein the overlaying act is performed from a fluoro sequence that captures both the wire tip and the vessel seen with a contrast agent.

8. The method according to claim 1, wherein the overlaying act is performed in a section of a fluoro sequence where a contrast agent puff has occurred but before the wire tip has entered the vessel.

9. The method according to claim 1, wherein the overlaying act is performed in a corresponding angiographic image.

10. The method according to claim 1, wherein a size of the wire tip obtained from the X-ray fluoro image is compared with an actual size of the wire tip.

11. The method according to claim 10, further comprising an act of estimating foreshortening of the vessel.

12. The method according to claim 10, further comprising an act of estimating an angle of the wire tip.

13. An X-ray imaging system comprising:
   an imager configured to obtain an X-ray fluoro image of a wire tip of a guide wire introduced into a vessel; and
   a processor configured to perform a method of providing support to percutanerous coronary intervention (PCI) device sizing of a lesion comprising acts of:
   detecting the wire tip on the fluoro image;
   segmenting and modeling the wire tip when it passes through the vessel;
   computing a virtual ruler;
   overlaying the computed virtual ruler with a first image displayed on a display; and
   providing sizing information of the lesion.

* * * * *